United States Patent [19]

Fowles et al.

[11] Patent Number: 4,524,231
[45] Date of Patent: Jun. 18, 1985

[54] PRODUCTION OF DURENE FROM ALCOHOLS AND ETHERS

[75] Inventors: Patrick E. Fowles, Doylestown; Tsoung-Yuan Yan, Philadelphia, both of Pa.

[73] Assignee: Mobil Oil Corporation, New York, N.Y.

[21] Appl. No.: 656,010

[22] Filed: Oct. 1, 1984

Related U.S. Application Data

[63] Continuation of Ser. No. 536,575, Sep. 29, 1983, abandoned, which is a continuation of Ser. No. 410,156, Aug. 20, 1982, abandoned.

[51] Int. Cl.³ .............................................. C07C 1/04
[52] U.S. Cl. .................................... 585/469; 585/408; 585/640; 585/733; 585/812; 585/814
[58] Field of Search .............. 585/408, 469, 640, 733, 585/814, 812

[56] References Cited

U.S. PATENT DOCUMENTS

| | | | |
|---|---|---|---|
| 2,560,373 | 7/1951 | Shmidl | 585/812 |
| 2,665,316 | 7/1954 | Bennett | 585/812 |
| 2,766,310 | 10/1956 | Bennett | 585/812 |
| 2,776,328 | 1/1957 | Bennett | 585/812 |
| 2,837,584 | 6/1958 | Hoff | 585/814 |
| 2,874,200 | 2/1959 | Sanford | 585/812 |
| 3,113,982 | 12/1963 | Dresser | 585/812 |
| 3,894,105 | 7/1975 | Chang et al. | 585/812 |

OTHER PUBLICATIONS

*Solubility of Durene and Isodurene at Low Temperatures,* Nakamura et al, *Journal of Industrial Chemistry,* vol. 71, No. 11, pp. 1,851–1,855 (1968).
*Trimellitic and Pyromellitic Anhydrides,* Harold W. Scheeline, Nov. 1970, Stanford Research Institute, Menlo Park, California.

*Primary Examiner*—D. E. Gantz
*Assistant Examiner*—A. Pal
*Attorney, Agent, or Firm*—Alexander J. McKillop; Michael G. Gilman; Dennis P. Santini

[57] ABSTRACT

Durene is recovered from a mixture rich in durene and containing hydrocarbons boiling in the gasoline range by cooling the mixture to a point where crystallization occurs and separating the crystallized durene. The durene subsequently is washed with a wash fluid. The wash fluid which can be methanol, is returned to a process wherein it is converted to gasoline and durene. The separated mother liquor is added to the gasoline fraction. The original mixture of durene and gasoline is obtained by the catalytic conversion of alcohols and ethers.

16 Claims, 1 Drawing Figure

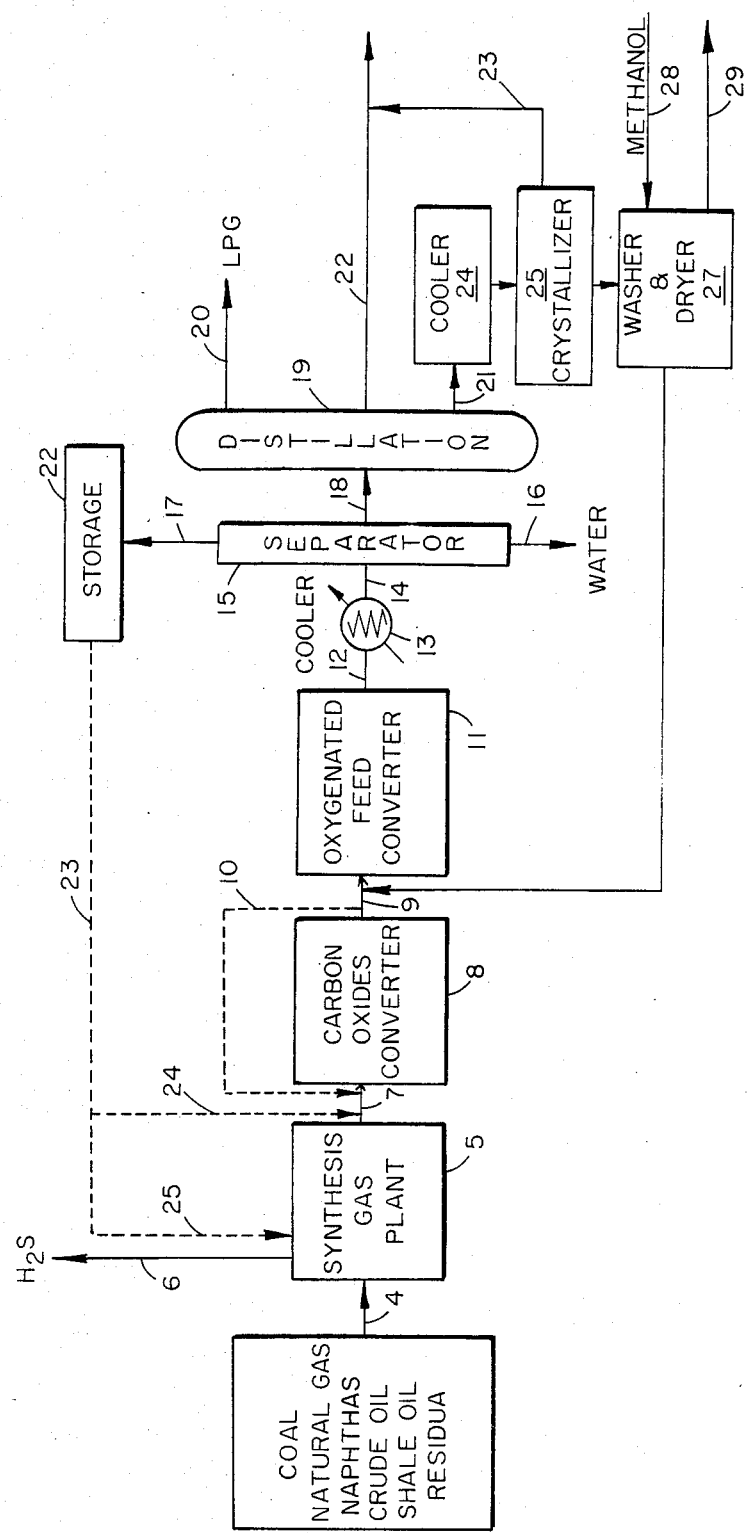

PRODUCTION OF DURENE FROM ALCOHOLS AND ETHERS

This application is a continuation of application Ser. No. 536,575, filed Sept. 29, 1983, which is a continuation of application Ser. No. 410,156, filed Aug. 20, 1982, both abandoned.

NATURE OF THE INVENTION

This invention relates to the production of tetraalkyl benzene, particularly durene, 1,2,4,5-tetramethylbenzene from sources such as methanol or synthesis gas. In another aspect this invvention relates to the coproduction of durene and gasoline from sources such as synthesis gas and methanol.

DESCRIPTION OF THE PRIOR ART

Of the tetraalkyl benzene isomers the most important one currently is durene, 1,2,4,5-tetramethylbenzene. Durene is an important intermediate in the preparation of pyromellitic anhydride used in the manufacture of polyimide resins. These resins are used in the aerospace industry, as electrical wire coatings, and in laminate applications. Until recently durene has been produced by crystallizing it from hydrocarbon fractions such as naphtha reformate fractions boiling in the range between about 350° F. and 425° F. U.S. Pat. Nos. 2,914,582; 2,914,586; and 3,150,197 are directed to aspects of this type of recovery.

Processes utilizing crystalline zeolites for converting synthesis gas as well as alcohols (primarily methanol) to gasoline have now been established in the art. In the conversion of synthesis gas to gasoline, synthesis gas is contacted in a first stage with a catalyst to form oxygenated compounds such as methanol and dimethyl ether. These products are then converted into hydrocarbons boiling in the gasoline range by passing them through a second catalytic bed containing a selected crystalline zeolite. U.S. Pat. Nos. 3,894,102 and 4,076,761 exemplify such a process and are incorporated herein by reference.

In two-stage processes for converting lower alcohols and ethers, such as methanol, ethanol, propanol, dimethyl ether, diethyl ether or mixtures thereof to gasoline these materials are contacted with a catalyst to produce a mixture having predominantly aliphatic or organic intermediate products. In a second stage this product with or without further modification is contacted with a catalyst such as crystalline zeolite and converted to a final product having a preponderance of hydrocarbons boiling within the range of gasoline and distillate. Such a process is exemplified in U.S. Pat. Nos. 3,928,483 and 3,894,105 which are incorporated herein by reference. Gasoline produced by this process ordinarily contains durene. Excessive amounts of durene in gasoline can be troublesome. Because durene is a solid at normal temperatures and pressures with a melting point of 175° F., it may crystallize out of the gasoline in unheated transfer lines or in storage tanks. Accordingly, it is highly desirable to remove the durene from the gasoline product or at least reduce the durene concentration.

OBJECTS OF THE INVENTION

One object of this invention is to provide an improved process for producing durene from syngas and/or methanol. Another object of this invention is to enable the coproduction of durene and gasoline. A further object of this invention is the recovery of durene from gasoline to improve the quality of gasoline. Another object of this invention is to provide a process for purifying recovered durene to a level required for its commercial use.

DESCRIPTION OF THE DRAWING

The attached FIGURE is a flow sheet for one embodiment of the process of this invention.

SUMMARY OF THE INVENTION

This invention is particularly novel and useful in that it makes use of a novel feedstock unusually rich in durene. It has hitherto been the practice to recover only as much durene as necessary to meet gasoline specifications. This process enables a greater recovery of durene and the simultaneous production of durene-free gasoline.

In its broadest aspect this invention comprises a process for separating a mixture of durene and hydrocarbons boiling in the range of gasoline in which the mixture is first fractionated into at least two fractions, one fraction, a heavy or bottoms fraction, being particularly concentrated in durene. This fraction ordinarily will be the higher fraction having a heavier boiling point. The remaining fraction or fractions will ordinarly constitute gasoline products. The heavy or bottoms fraction is cooled to a temperature at which durene begins to crystallize. The crystallized durene is separated from the mother liquor. In a modification of this broad aspect, the separated crystalline durene is washed with a solvent to remove residual mother liquor and the solvent is returned to a process stream where it is converted to additional gasoline or other hydrocarbons. In another aspect, this invention comprises a process for making durene from synthesis gas comprising contacting the synthesis gas with a catalyst thereby converting the synthesis gas to a mixture of ethers, alcohols and hydrocarbons, contacting the mixture with a second catalyst thereby converting the mixture to a stream rich in durene and hydrocarbons boiling within the range of gasoline and then further distilling the product stream to provide a bottoms product concentrated in durene and an ovearhead product comprising gasoline. The durene is removed from the product as described above and below. In still another aspect this invention comprises a process for manufacturing durene wherein alcohols and/or ethers are contacted with a catalyst and converted to a mixture rich in durene and gasoline. This mixture is then separated into gasoline and crystallized durene. The description below is divided into three main sections. The first two sections describe respectively the conversion of synthesis gas and the conversion of methanol each to a product stream containing gasoline and durene. It will be readily apparent that similar product streams are available from other sources such as those described in U.S. Pat. Nos. 2,914,582; 2,914,586 and 3,150,197. The third section describes the gasoline/durene separation step which is combined with either of the processes described in the first two sections or is applied to other available process streams.

DESCRIPTION OF THE INVENTION

CONVERSION OF SYNTHESIS GAS TO A MIXTURE OF DURENE AND GASOLINE

In accordance with the stated objects of this invention, one aspect of this invention is to provide a process for converting syngas to durene and hydrocarbon fuels. To accomplish this objective, coal or other fossil fuel is gasified to form synthesis gas (a mixture of carbon monoxide and hydrogen). Techniques for deriving synthesis gas from coal, natural gas, naphthas, crude oil, shale oil and residua are well known. If desired the gas is adjusted by one of several means to provide a predetermined volumetric ratio of hydrogen to carbon monoxide plus carbon dioxide. The synthesis gas is then contacted with a carbon monoxide reduction catalyst in a first reaction zone to produce a reduction product containing a satisfactory concentration (i.e. 20 weight percent) of ethers, alcohols, and other hydrocarbon products. The reduction product is catalytically converted by contact with a catalyst which preferably is a crystalline zeolite of the ZSM-5 type to form a major fraction of aromatics-rich high octane gasoline and a lesser fraction of useful products that include durene and a hydrogen-rich gaseous mixture that may be recycled to the fossil fuel gasifier.

Representative of the ZSM-5 type zeolites are ZSM-5, ZSM-11, ZSM-23, ZSM-35 and ZSM-38. ZSM-5 is disclosed and claimed in U.S. Pat. No. 3,702,886 and U.S. Pat. No. RE. 29,948, ZSM-11 is disclosed and claimed in U.S. Pat. No. 3,709,979. Also, see U.S. Pat. No. 3,832,449 for ZSM-12; U.S. Pat. No. 4,076,842 for ZSM-35; U.S. Pat. No. 4,106,245 for ZSM-35 and U.S. Pat. No. 4,406,839 for ZSM-38. The disclosures of these patents are incorporated herein by reference.

Reference is now made to the attached FIGURE which illustrates this invention in certain of its aspects, without being limited thereto. Coal, natural gas, naphthas, crude oil shale oil, or residua, or a combination thereof, is conveyed via line 4 to the synthesis gas plant, 5, where it is converted to synthesis gas. If hydrogen sulfide is produced in this plant, it may be separated and sent via line 6 to a treatment plant (not shown) for sulfur recovery. Synthesis gas, previously treated in a catalytic carbon monoxide shift converter and then reduced in carbon dioxide content by selective sorption, is conveyed via line 7 to a first reaction zone 8, where it is at least partially converted catalytically to produce a carbon monoxide reduction product that contains at least 20% by weight of alcohols, ethers and other hydrocarbon products. Part or all of the unconverted synthesis gas may be separated from such reduction product and recycled via line 10, but it is preferred to convey the total mixture via line 9 to the second reaction zone 11 where catalytic conversion to hydrocarbons and steam occurs. The reaction products from the second reaction zone 11 are conveyed via line 12 to a cooler, 13, and the cooled products are then conveyed via line 14 to a separator 15; note that the cooler 13 and line 14 and separator 15 may be one integral unit. Water is removed from separator 15 via line 16, gases via line 17, and liquid hydrocarbon products via line 18. The liquid hydrocarbon products are conveyed via line 18 to a distillation tower 19. In distillation tower 19 the liquid hydrocarbon products are fractionated into an overhead product of propane and butanes (LPG), an intermediate gasoline cut and a heavier gasoline cut, which is rich in durene. This heavier-durene cut has a boiling point above about 330° F. to 380° F. (165° C. to 195° C.). The actual temperature at which this cut is made will depend in part on how much durene it is desired to recover. It is this cut which is processed further to separate the durene therefrom.

PRODUCTION FROM METHANOL

In another aspect of this invention the feedstock of gasoline and durene processed in the crystallization-washing phase is derived from $C_1$–$C_3$ alcohols. These alcohols are converted to a stream of highly aromatic gasoline containing durene by a process which preferably is a multi-stage process. In the first stage the alcohol reactant is contacted with a condensation catalyst to produce a predominantly aliphatic organic intermediate product. In the second stage the intermediate product with or without further modification is contacted with a crystalline zeolite preferably of the ZSM-5 type to convert the intermediate product to a final product which is a hydrocarbon mixture having a preponderance of normally fluid hydrocarbons in the gasoline boiling range of up to 415° F.

The lower alcohols that may be charged to the process of this invention, or more specifically to the first stage of the process include methanol, ethanol, normal propanol and isopropanol or their corresponding ethers. This feed may consist of a relatively pure single alcohol or ether or mixture of these with one another. The preferred charge is to this first stage of the process is ethanol and/or methanol. Particularly preferred are charges containing substantial fractions of methanol. Mixtures of methanol and dimethylether are also included as preferred charges.

In the first stage of this conversion process the alcohol reactant is contacted with a condensation catalyst to produce water and a predominantly aliphatic organic intermediate product. The condensation catalyst may be any catalyst which results in the intermolecular dehydration of the alcohol reactant to form an aliphatic product of higher carbon to oxygen ratio than the feed. Solid inorganic and organic acidic catalysts such as phosphoric acid supported on kieselguhr, high surface area silica-alumina, acidic alumina, acid treated clays, bauxite and polystyrene sulfonic acids of the ion exchange type can be used.

The predominantly aliphatic intermediate, for example, dimethylether produced in the first stage of this process, without further conversion is contacted with a crystalline zeolite which preferably is selected from the group consisting of ZSM-5, ZSM-11, ZSM-12, ZSM-21 and TEA Mordenite. Of these ZSM-5 is particularly preferred. Operating conditions for this process are disclosed in U.S. Pat. No. 3,928,483. As disclosed in this patent, it may also be desirable to follow the initial alcohol condensation stage by a further conversion stage. This intermediate conversion can be carried out in the effective presence of either the same catalyst as used for the first stage, or deactivated last stage catalyst.

The reaction product from the last stage of the reaction will contain aliphatic and aromatic gasoline boiling-range hydrocarbons mixed with durene. This is the product stream to be processed in the separation-crystallization step described below.

CRYSTALLIZATION AND WASHING

The primary feature of the process of this inventions is the series of steps wherein a liquid mixture of durene and gasoline preferably containing at least between 10 to 30 percent by weight of durene is separated into at least two fractions, preferably distillation, to provide a lower boiling fraction or fractions that will constitute primarily the gasoline product and will be processed as may be further desired to convert it to a final gasoline product. The higher boiling point fraction preferably has a boiling point of at least 300° F. (150° C.) and preferably above 330° F. (165° C.). It represents a fraction sufficiently concentrated in durene so that as it is further cooled or chilled durene begins to crystallize. Referring again to the drawing, at line 21, the heavier gasoline cut is diverted through a heat exchanger (not shown) and from thence into a crystallization system (cooler 24 and crystallizer 25) wherein the gasoline-durene mixture is cooled to a temperature sufficient to induce the durene present to crystallize, thereby forming a mixture of durene crystals and mother liquor. With the process described the stream is suprisingly rich in durene and low in durene isomers which are difficult to separate. As a result the durene crystallizes out at a relatively high temperature of about 100° F. For efficient operation for durene recovery a temperature of 32° F. to 100° F. (0° C. to 40° C.) can be used but a temperature of 65° F. to 80° F. (15° C. to 30° C.) is preferred.

In the practice of this invention durene crystals of excellent quality are obtained which facilitates their recovery and further purification. The crystalline durene is then separated from the mother liquor by centrifugation, filtration or other suitable means. The separation step is preferably conducted at the crystallization temperature or only slightly thereabove to prevent loss of durene to the solubilizing mother liquor. The mother liquor occluded on the surface of the durene can be removed by washing the separated crystals with a solvent, preferably methanol. The step of washing is done at temperature of 65° F. to 80° F. Methanol is preferred as a wash solvent because it can be recycled to a point upstream of the oxygenated feed converter 11 and processed as part of the feed stream to the converter 11. Methanol thus requires no separate recovery system as might other solvents. Other wash solvents which can be used include lower aliphatic hydrocarbons such as paraffins, olefins, alcohols, keytones, ethers, esters and cyclic hydrocarbons. Examples include propane, butane, pentane, propene and cyclopentane. Examples of solvents which, like methanol, can be recycled to the ether alcohol feed converter include ethanol, propane and dimethylether. The washed crystalline durene product can have a purity as high as 96% or higher meeting the requirements for commodity grade durene.

The quantity of wash liquid necessary to remove the mother liquor adsorbed or occluded on the durene crystals depends to a large extent upon the degree of purity desired and the particular solvent utilized. Generally the quantity of washed liquid varies between 5 and 200 weight percent of the durene. A preferred range is between 10 and 50 weight percent however. The durene crystals can be washed with solvent in batch wise or continuous fashion with recycle of the mother liquor when advantageous. After the washing step the crystallized durene is dried and is processed as may be desired further. To decrease the volume of the durene product and consequently packaging cost the durene can be melted before packaging.

As noted previously the source of the mixture of durene and gasoline boiling range hydrocarbons can be derived from a number of processes. Primary among these processes will be the conversion of synthesis gas to gasoline boiling range hydrocarbons and the conversion of methanol to gasoline. Either one of these processes will result in the feedstock to be processed as described previously.

Having described the invention, the following example is given to illustrate the invention without limiting the scope thereof. Parts and percentages are by weight unless expressly stated otherwise and the reference numerals designate parts of the flow sheet previously discussed.

EXAMPLE

A feed stream of ethers, alcohols and other hydrocarbons is introduced into converter 11 and converted to an aromatic stream containing approximately 8% of durene. The stream is passed through cooler 13 and into separator 15 where the liquid aromatic product is recovered and passed into the distillation tower 19. In distillation tower 19 the aromatic product obtained is fractionated into an overhead stream, a light gasoline stream and a heavier gasoline stream. The distillation column operates at a temperature of between 340° F. and 350° F. and a pressure of 0 psig. The heavier gasoline product emerging from the distillation column 19 through line 21 contains a concentration of between 40 and 60% of durene. It is desired in this case to remove approximately 50% of the durene from the heavier gasoline product to meet the durene concentration limitation of the gasoline pool. All product is removed through line 21 and passed through the crystallization system. If preferred not all the product need be carried in line 21 but a separately boiling fraction can be carried off through line 22 and treated further such as by hydrotreating to form a desired gasoline product. The product stream is passed first through a crystallizer 25 operating at a temperature of 70° F. (20° C.) where the crystallized durene is recovered and washed at 27 with methanol at a temperature of about 70° F. The crystallized durene is then removed and dried yielding a product of 97% purity. The effluent wash liquid from the washing operation is passed back into the methanol conversion system through line 26.

What is claimed is:

1. A method for producing durene from a feed mixture comprising $C_1$–$C_3$ alcohols or ethers or mixtures thereof comprising:
   (a) catalytically converting said feed mixure to a product stream comprising durene and liquid hydrocarbons boiling in the gasoline boiling range by contacting said feed mixture with a crystalline zeolite in a reaction zone;
   (b) fractionating the stream of (a) to provide at least one lower boiling point fraction boiling below about 150° C. to about 165° C. and a higher point fraction boiling above about 150° C. to about 165° C.;
   (c) cooling said higher boiling point fraction to a temperature between about 30° C. and about 0° C.;
   (d) crystallizing durene from said cooled fraction of (c);
   (e) separating crystallized durene from said fraction leaving behind a mother liquor; and
   (f) returning said mother liquor to the lower boiling point fraction of (b).

2. The method of claim 1 wherein the separated crystallized durene of (e) is washed with a solvent and said solvent is thereafter converted to a product stream comprising a mixture of durene and liquid hydrocarbons boiling in the gasoline boiling range.

3. The method of claim 1 wherein separated crystallized durene of (e) is washed with a solvent and said solvent is thereafter converted catalytically to a product stream comprising a mixture of durene and liquid hydrocarbons and said product stream constitutes a part of the product stream subjected to fractionation in (b).

4. The method of claim 1 wherein the separated crystallized durene of (e) is washed with a solvent and said solvent is thereafter added to said feed mixture flowing to said reaction zone.

5. The method of claim 1 wherein said stream of (a) is fractionated into two fractions, one boiling below and the other above about 165° C. to about 195° C.

6. The method of claim 1 wherein said higher boiling point fraction of (b) is cooled to a temperature of between about 15° C. and about 30° C.

7. The method of claim 1 wherein the crystallized durene from (e) is consolidated by melting it.

8. The method of claim 2, wherein said solvent is selected from the group consisting of propane, butane, pentane, propene and cyclopentane.

9. The method of claim 3, wherein said solvent is selected from the group consisting of propane, butane, pentane, propene and cyclopentane.

10. The method of claim 4 wherein said solvent is selected from the group consisting of propane, butane, pentane, propene and cyclopentane.

11. The method of claim 2 wherein said solvent is selected from the group consisting of methanol and dimethyl ether.

12. The method of claim 3, wherein said solvent is selected from the group consisting of methanol and dimethyl ether.

13. The method of claim 4 wherein said solvent is selected from the group consisting of methanol and dimethyl ether.

14. A method for producing durene from a feed mixture comprising $C_1$-$C_3$ alcohols, ethers or mixtures thereof comprising:
 (a) catalytically converting said feed mixture in a first reaction zone to a predominantly aliphatic organic intermediate product;
 (b) converting said intermediate product in a second reaction zone comprising a zeolite selected from the group consisting of ZSM-5, ZSM-11, ZSM-23, ZSM-35 and ZSM-38 to a product stream comprising durene and liquid hydrocarbons boiling in the gasoline boiling range;
 (c) fractionating the product stream from (b) into at least one lower boiling point fraction boiling below about 150° C. to about 165° C. and a higher boiling point fraction boiling above about 150° C. to about 165° C.;
 (d) cooling said higher boiling point fraction to a temperature between about 15° C. and about 30° C.;
 (e) crystallizing durene from said cooled fraction of (d);
 (f) separating crystallized durene from said fraction leaving behind a mother liquor; and
 (g) returning said mother liquor to the lower boiling point fraction of (c).

15. The method of claim 14 wherein the zeolite is ZSM-5 zeolite.

16. The method of claim 14 wherein the product stream of (b) contains at least 10 percent by weight of durene.

* * * * *